(12) United States Patent
Kawakami et al.

(10) Patent No.: US 7,676,381 B2
(45) Date of Patent: Mar. 9, 2010

(54) MEDICAL SUPPORT SYSTEM

(75) Inventors: Youichi Kawakami, Tondabayashi (JP);
Toshiharu Noro, Yokohama (JP);
Kosuke Sasai, Kobe (JP)

(73) Assignee: Konica Minolta Holdings, Inc., Tokyo (JP)

( * ) Notice: Subject to any disclaimer, the term of this patent is extended or adjusted under 35 U.S.C. 154(b) by 1092 days.

(21) Appl. No.: 11/304,152

(22) Filed: Dec. 15, 2005

(65) Prior Publication Data
US 2006/0143046 A1 Jun. 29, 2006

(30) Foreign Application Priority Data
Dec. 28, 2004 (JP) .............................. 2004-378608

(51) Int. Cl.
*G06Q 10/00* (2006.01)
(52) U.S. Cl. .............................................. 705/2; 705/3
(58) Field of Classification Search ................ 705/2–4; 600/300–301
See application file for complete search history.

(56) References Cited

U.S. PATENT DOCUMENTS

| | | | |
|---|---|---|---|
| 7,010,519 B2* | 3/2006 | Tada et al. ...................... | 707/3 |
| 7,437,373 B2* | 10/2008 | Whitehead .................. | 707/100 |
| 2001/0051881 A1* | 12/2001 | Filler .............................. | 705/3 |
| 2003/0055816 A1* | 3/2003 | Paine et al. ..................... | 707/3 |
| 2004/0172292 A1* | 9/2004 | Takekoshi et al. .............. | 705/2 |
| 2006/0020492 A1* | 1/2006 | Cousineau et al. ............. | 705/2 |
| 2006/0095298 A1* | 5/2006 | Bina ............................. | 705/2 |
| 2006/0253431 A1* | 11/2006 | Bobick et al. ................. | 707/3 |

FOREIGN PATENT DOCUMENTS

JP 10-031615 2/1998

* cited by examiner

*Primary Examiner*—Vivek D Koppikar
(74) *Attorney, Agent, or Firm*—Brinks Hofer Gilson & Lione

(57) ABSTRACT

The present invention provides a medical support system capable of properly supporting entry of medical information by a medical professional. A medical support system stores, as medical data, first medical information entered by a medical professional as an operator, and second medical information entered without direct intervention of the medical professional. Further, the medical support system generates and outputs support information for supporting entry of the first medical information by the medical professional. In the medical support system, the support information is generated on the basis of the first medical information and second medical information being entered. Therefore, in the medical support system, when the first medical information and second medical information being entered changes, the support information to be generated also changes.

18 Claims, 14 Drawing Sheets

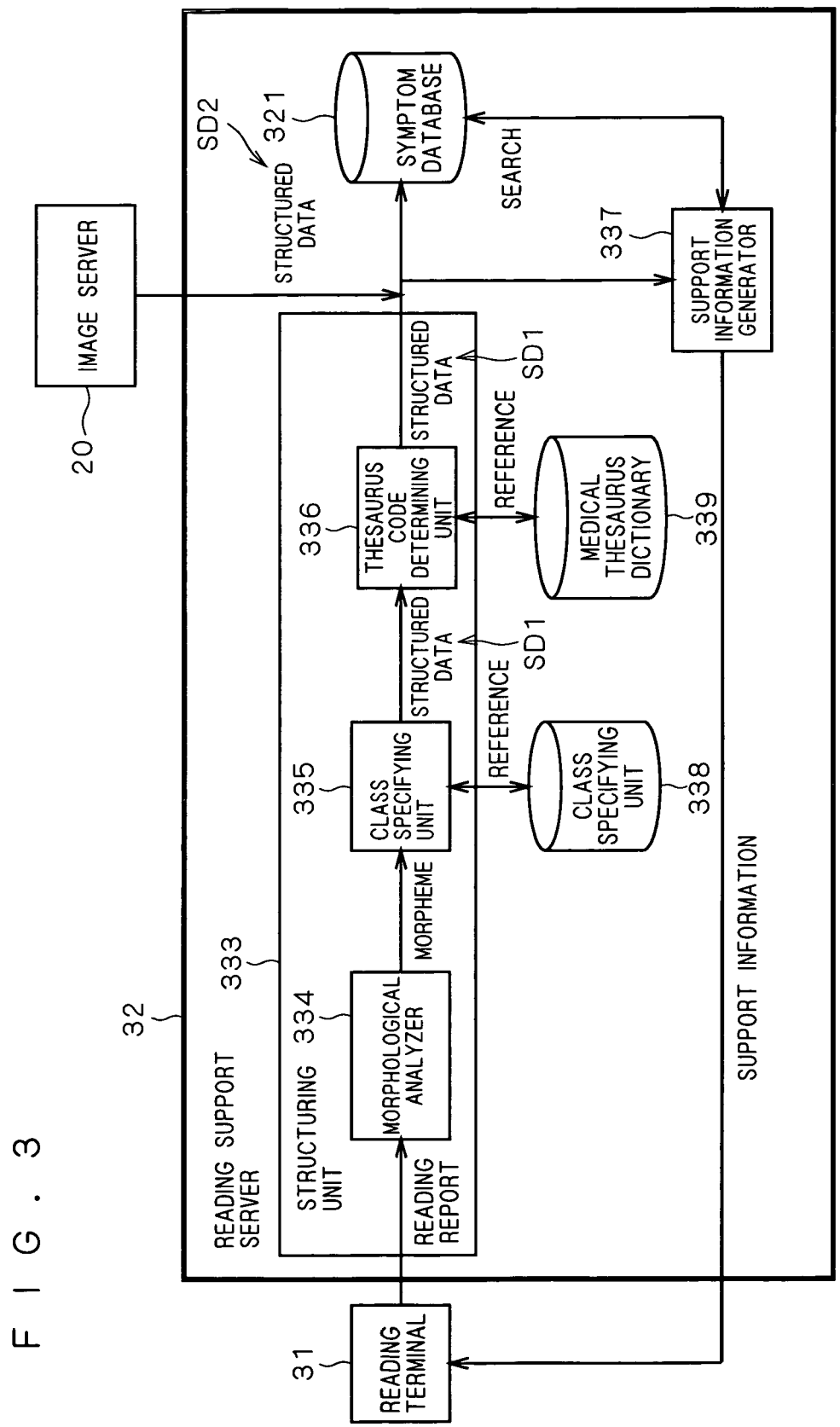
F I G . 3

EXAMPLE OF STRUCTURED DATA OF READING REPORT

| WORD | CLASS |
|---|---|
| LUNG | REGION |
| IN | (NONE) |
| SHADE | SYMPTOM |
| IS | (NONE) |
| SEEN | (NONE) |

EXAMPLE OF READING REPORT ENTRY SCREEN

EXAMPLE OF REGISTRATION CONFIRMATION SCREEN

EXAMPLE OF DIAGNOSIS SUPPORT MENU
(NO ENTRY IN REMARK ENTRY BOX)

EXAMPLE OF DIAGNOSIS SUPPORT MENU
(WITH DATA ENTERED IN REMARK ENTRY BOX)

FIG. 13

```
PATIENT: LIST OF REPORTS OF YUSUKE MATSUMIYA

DATE         REGION                    REMARKS 2004-10-04   HEAD SCREENING CT    SYMPTOM UNCHANGED ···
2004-09-27   HEAD SCREENING CT    SEEMS TO HAVE JUGULAR ELEVATION ···
2004-09-10   HEAD SCREENING CT    ABNORMALITY IS SEEN IN JUGULAR FORAMEN···

[ DISPLAY DETAILS ]
```

INF11     EXAMPLE OF DIAGNOSIS SUPPORT INFORMATION    BT

FIG. 14

```
REPRESENTATIVE READING REPORT IN HEAD SCREEN CT

DATE              DIAGNOSIS            AGE    SEX 2004-09-27   HIGH POSITION OF JUGULAR BULB   25   MALE
2004-09-17             ANEURYSM              43   MALE
2004-08-10       GLOMUS JUGULARE TUMOR       55   MALE

[ DISPLAY DETAILS ]
```

INF12     EXAMPLE OF DIAGNOSIS SUPPORT INFORMATION    BT

FIG. 15

```
SIMILAR IMAGE

DATE              DIAGNOSIS              IMAGE 2004-09-27    HIGH POSITION OF JUGULAR BULB
  2004-11-17          ANEURYSM
  2004-08-10    GLOMUS JUGULARE TUMOR
                                         DISPLAY DETAILS
```

EXAMPLE OF DIAGNOSIS SUPPORT INFORMATION

INF13

FIG. 16

```
     ANOTHER READING REPORT ON JUGULAR VEIN

DATE              DIAGNOSIS           AGE      SEX 2004-09-27   HIGH POSITION OF JUGULAR BULB   25    MALE
     2004-11-17   HIGH POSITION OF JUGULAR BULB   61    FEMALE
     2004-08-10   GLOMUS JUGULARE TUMOR           55    MALE

DISPLAY DETAILS
```

EXAMPLE OF DIAGNOSIS SUPPORT INFORMATION    BT

INF14

EXAMPLE OF ENTRY SUPPORT INFORMATION
INF15

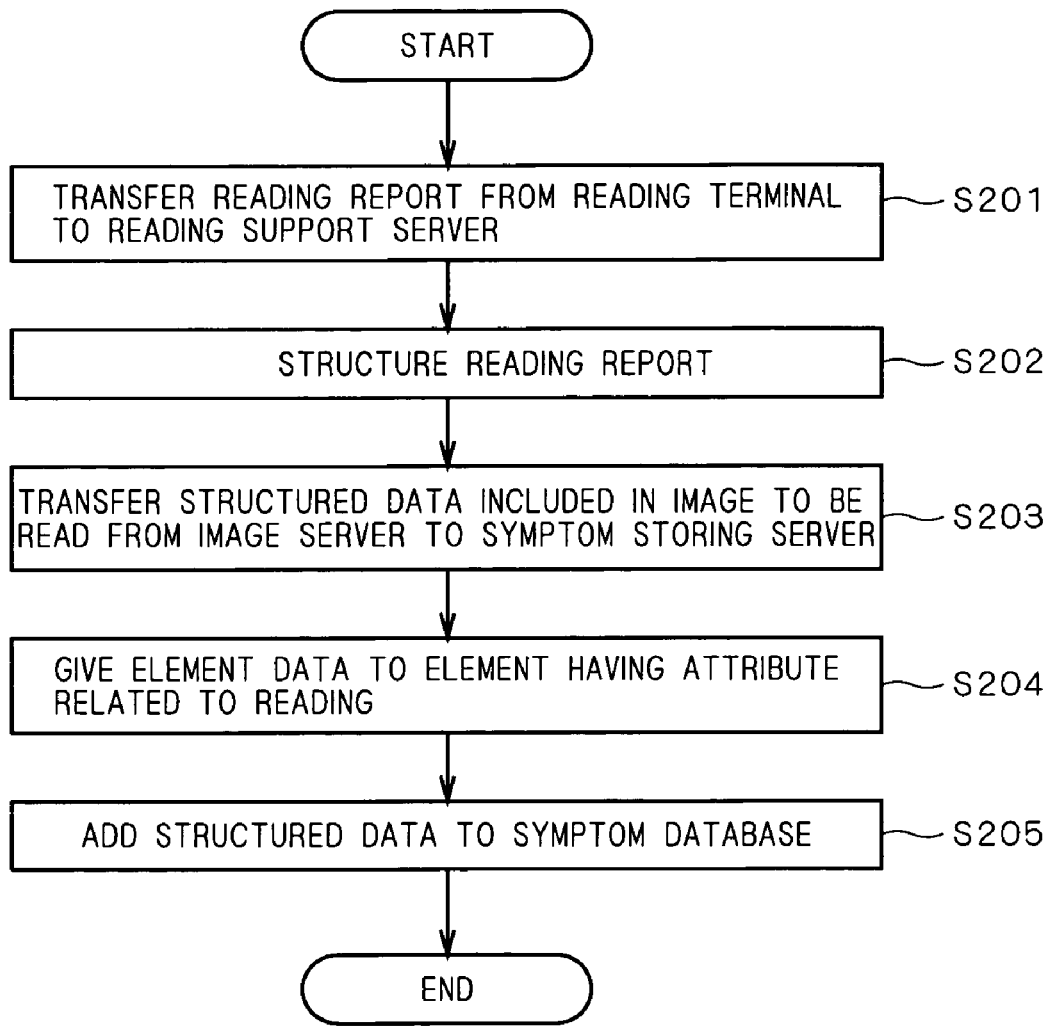

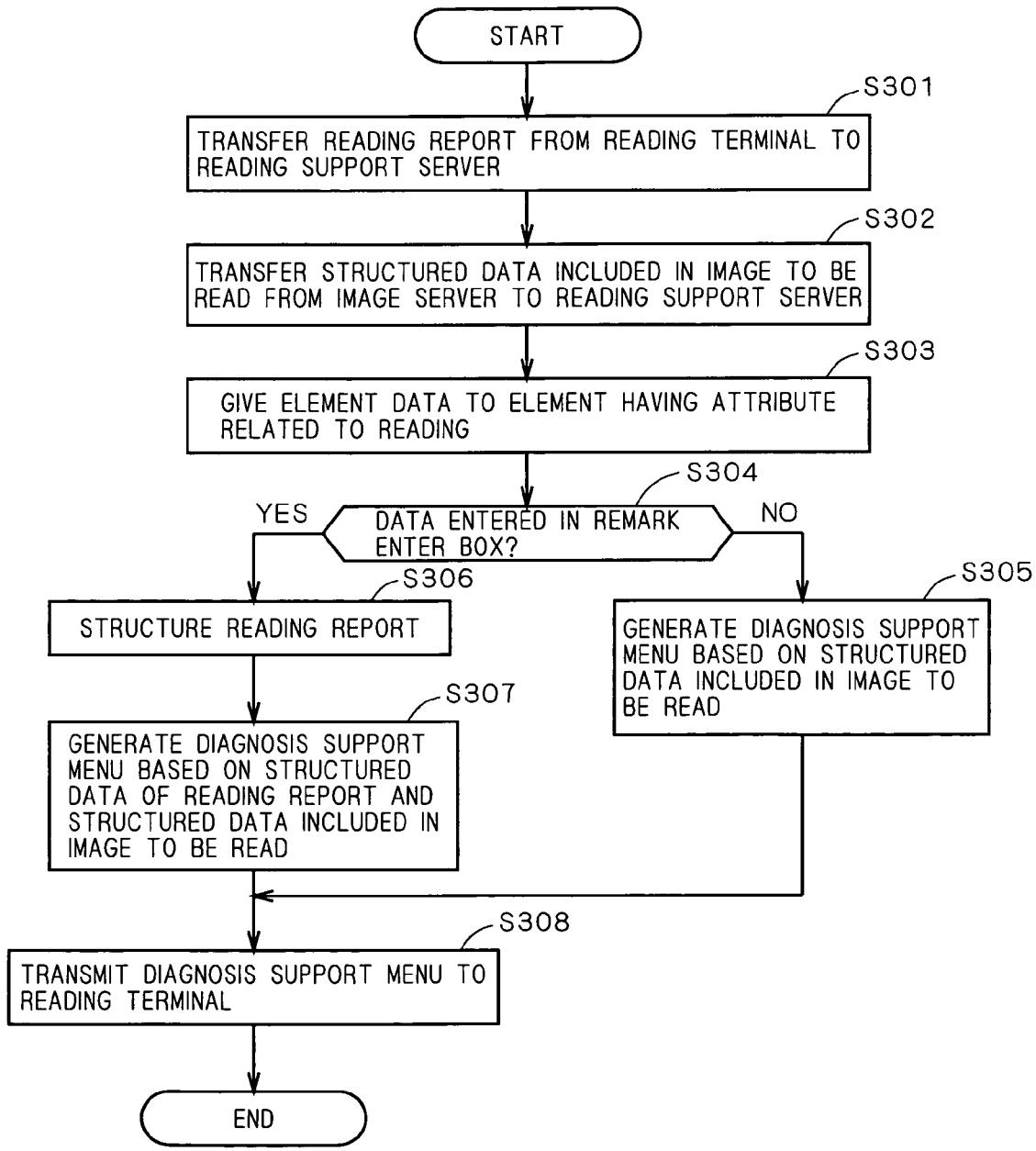

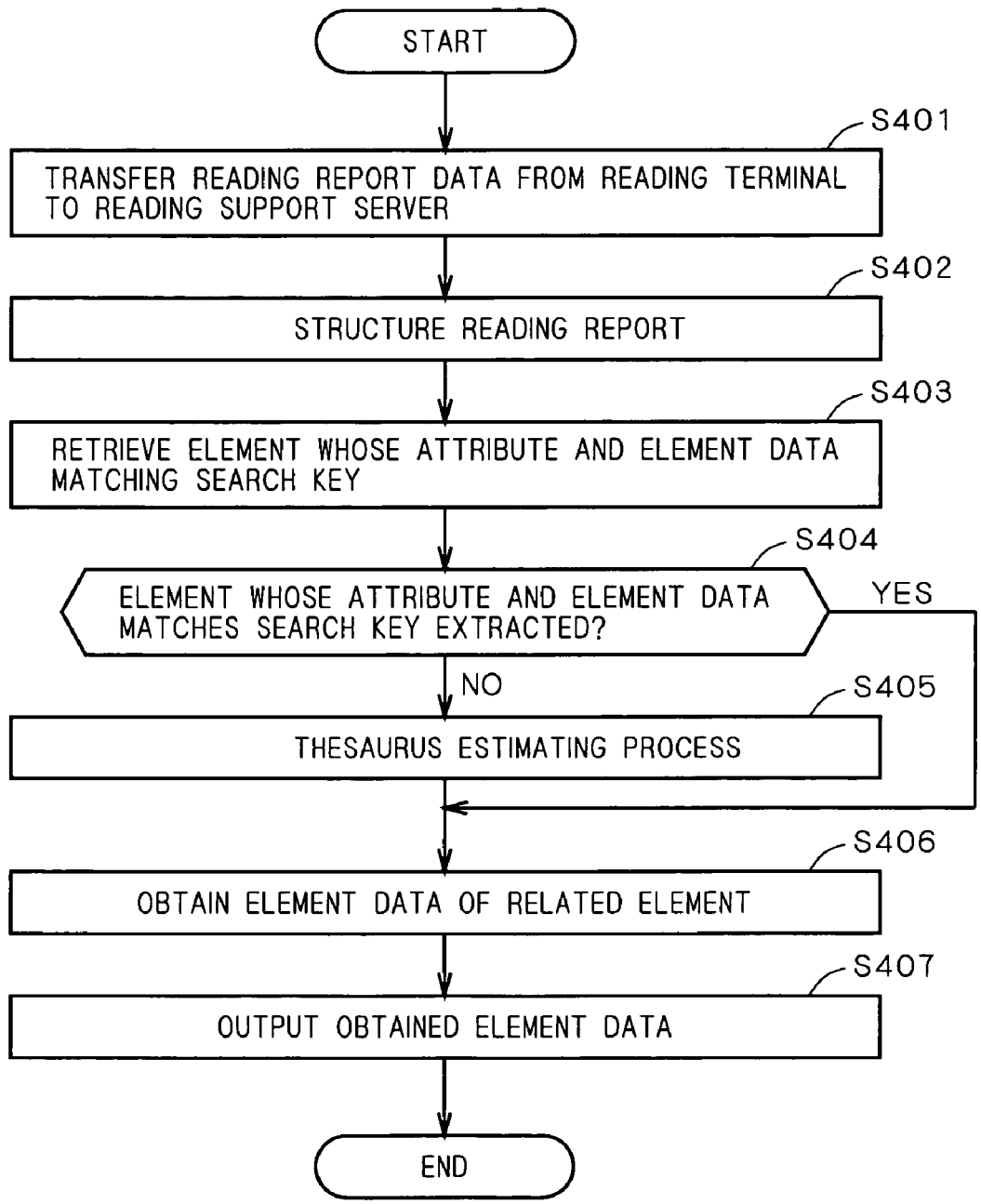

MEDICAL SUPPORT SYSTEM

This application is based on application No. 2004-378608 filed in Japan, the contents of which are hereby incorporated by reference.

BACKGROUND OF THE INVENTION

1. Field of the Invention

The present invention relates to a medical support system for supporting entry of medical information by a medical professional.

2. Description of the Background Art

Hitherto, a medical support system for supporting entry of medical information by a medical professional is used in the field of medical practice. For example, a medical support system for presenting, during entry of a diagnostic report of a patient, a diagnostic report of the same patient entered in the past is used in order to support entry of a diagnostic report by a doctor. Another medical support system is also used, which presents a predetermined template during entry of a diagnostic report, in order to support efficient entry of a diagnostic report by a doctor.

Japanese Patent Application Laid-Open No. 10-31615 (1998) relates to a technique for supporting navigation of a user.

In a conventional medical support system, however, information presented for support is generated irrespective of medical information being entered by a doctor and is therefore often useless. For example, although a doctor is entering a report on a gastric cancer, a template of a chest X-ray photograph or a slice picture of brain is presented by a medical support system.

SUMMARY OF THE INVENTION

The present invention relates to a medical support system for supporting entry of medical information by a medical professional.

According to the present invention, a medical support system includes: an input unit used for entering medical information; a storage for storing the medical information entered by using the input unit; and a generator for generating support information that supports entry of medical information by a medical professional in the input unit. Herein, the generator generates the support information on the basis of medical information being entered by the input unit. Since support information to be generated changes dynamically according to medical information being entered, entry of medical information by a medical professional can be properly supported.

Preferably, the generator generates the support information on the basis of character string information being entered as medical information by a medical professional. Since support information to be generated changes dynamically according to character string information being entered by a medical professional, entry of medical information by a medical professional can be supported more properly.

Preferably, the generator generates the support information on the basis of character string information on an image for medical use. Since support information to be generated changes dynamically according to character string information on an image for medical use, entry of medical information by a medical professional can be supported more properly.

It is therefore an object of the present invention to provide a medical support system capable of properly supporting entry of medical information by a medical professional.

These and other objects, features, aspects and advantages of the present invention will become more apparent from the following detailed description of the present invention when taken in conjunction with the accompanying drawings.

BRIEF DESCRIPTION OF THE DRAWINGS

FIG. 3 is a block diagram which illustrates the configuration of a reading support server;

FIG. 13 illustrates a reading report list display screen as the diagnosis support information;

FIG. 14 illustrates a reading report list display screen as the diagnosis support information;

FIG. 15 illustrates a reading report list display screen as the diagnosis support information;

FIG. 16 illustrates a reading report list display screen as the diagnosis support information;

FIG. 18 is a flowchart which shows an operation performed in the case of accumulating reading reports in the symptom database;

FIG. 19 is a flowchart which shows an operation performed in the case of generating diagnosis support information; and FIG. 20 is a flowchart which shows an operation performed in the case of generating entry support information.

DESCRIPTION OF THE PREFERRED EMBODIMENTS

1. Main Functions of Medical Support System

Figure 1:
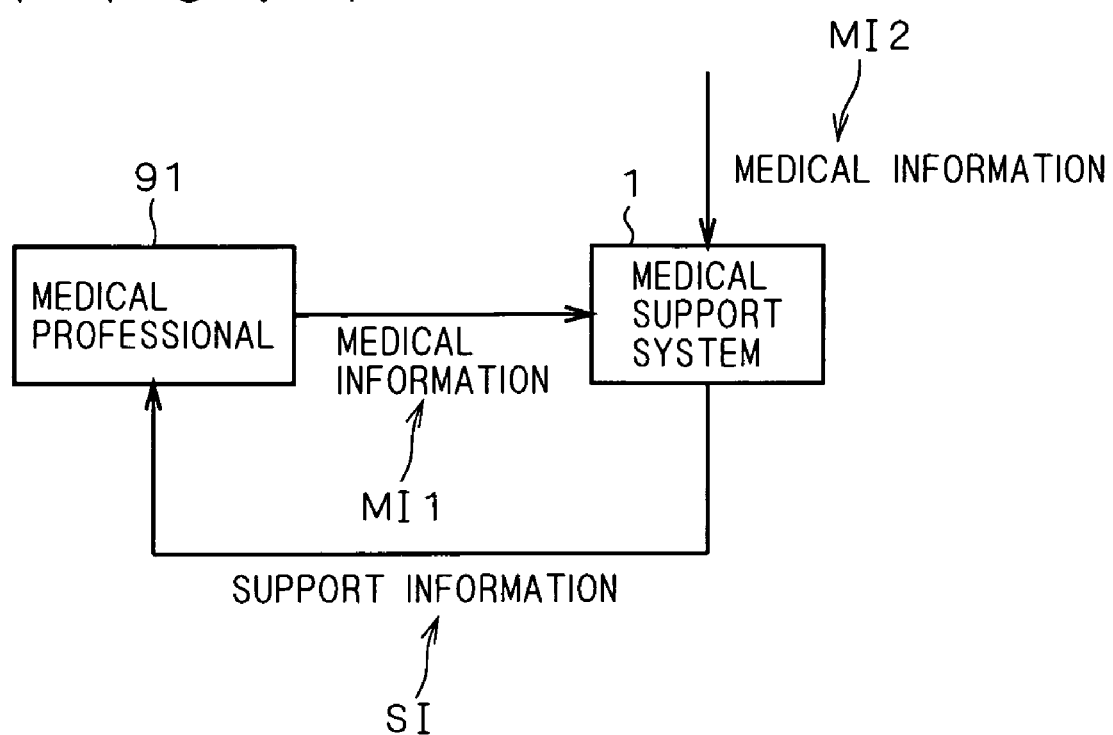
FIG. 1 illustrates main functions of a medical support system according to a preferred embodiment of the present invention.

FIG. 1 illustrates main fictions of a medical support system 1 according to a preferred embodiment of the present invention.

As illustrated in FIG. 1, the medical support system 1 stores medical information MI1 entered by a medical professional 91 as an operator, and medical information MI2 entered without direct intervention of the medical professional 91. Further, the medical support system 1 generates and outputs support information SI for supporting entry of the medical information MI1 by the medical professional 91. The support information SI includes information for supporting enrichment of contents of the medical information MI1 entered by the medical professional 91, and information for supporting improvement in entry speed of the medical information MI1 by the medical professional 91.

In the medical support system 1, the support information SI is generated on the basis of the medical information MI1 and medical information MI2 being entered. Therefore, when the medial information MI1 and medical information MI2 being entered change, the support information SI to be generated also dynamically changes. In such a medical support system 1, the support information SI to be generated changes dynamically according to the medical information MI1 and medical information MI2 being entered, so that entry of the medical information MI1 by the medical professional 91 can be properly supported.

Examples of the medical professional 91 supported by the medical support system 1 include a doctor, a nurse, a pharmacist, a hygienist, a maternity nurse, a radiation technologist, a clinical technologist, a medical technologist, a physical therapist, and an occupational therapist.

The "medical information MI1 entered by the medical professional 91" is medical information including character string information such as a diagnostic report describing a result of diagnosis by a doctor, a reading report describing a result of reading on a medical image by a doctor, a nursing report in which nursing activities of a nurse are recorded, and an incident report in which incidents that occurred during medical activities are recorded.

On the other hand, the "medical information MI2 entered without direct intervention of the medical professional 91 as an operator" is typically a medical image captured by an image diagnostic apparatus and character string information of the medical image, but the medical information MI2 may be other information. The medical information MI2 is entered to the medical support system 1 by using, for example, an electric communication line or a portable recording medium.

In the following, the configuration and operation of a reading support system for supporting entry of a reading report by a reading physician will be described as one example of such a medical support system 1. The reading support system to be described below is just an example of the medical support system 1 and other embodiments can be also employed.

2. Configuration of Reading Support System 2.1. General Configuration

Figure 2:
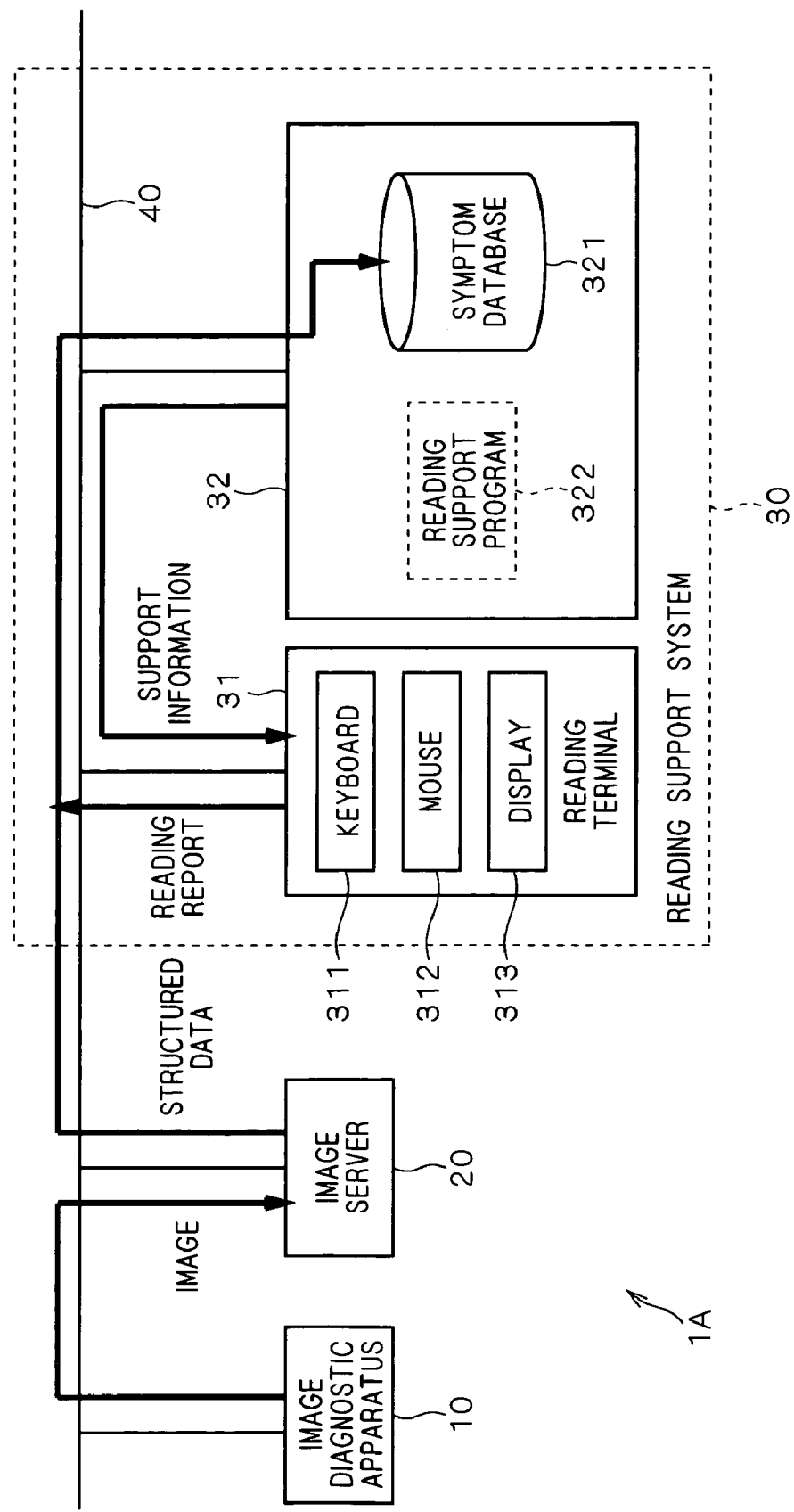
FIG. 2 is a block diagram which illustrates a general configuration of a medical image management system including a reading support system according to the preferred embodiment of the present invention.

FIG. 2 is a block diagram which illustrates a general configuration of a medical image management system (PACS: Picture Archiving and Communication System) 1A including a reading support system 30 according to a preferred embodiment of the present invention.

As illustrated in FIG. 2, the medical image management system 1A has at least one image diagnostic apparatus (modality) 10, an image server 20 and the reading support system 30 which are communicably connected to each other via a network 40.

The image diagnostic apparatus 10 is an image diagnostic apparatus such as an X-ray machine, a CT (Computed Tomographic) apparatus, a nuclear magnetic resonance image diagnostic apparatus, or an ultrasonic image diagnostic apparatus, and generates an image for medical use (hereinafter, simply referred to as "image").

The image server 20 accumulates (stores) an image (image file) generated by the image diagnostic apparatus 10. An image accumulated in the image server 20 is an image in a DICOM (Digital Image and Communications in Medicine) format, and includes structured data based on modeling of the DICOM.

In image diagnosis, generally, a doctor who introduces a patient to another doctor, a rendering doctor who generates an image, and a reading doctor who reads the image are different from each other. In image diagnosis, there may be a doctor in charge of recording who gives a patient primary medical care. In those cases, the reading doctor receives an order for image diagnosis through the doctor in charge of recording and the rendering doctor, and reads the image. In this preferred embodiment, image diagnosis order information is included in structured data that is included in an image, and the order information is used for generating support information.

The reading support system 30 has a reading terminal 31 and a reading support server 32. Each of the reading terminal 31 and the reading support server 32 is a computer having at least a CPU and a memory.

The reading terminal 31 acquires an image accumulated in the image server 20 and displays the image as an image to be read on a display 313 and, in addition, provides input means used for entering a reading report of the displayed image to a reading doctor. More concretely, the reading doctor can enter a reading report by using a character string (natural sentence) from the reading terminal 31 by performing GUI operation using a keyboard 311 and a mouse 312 while referring to a GUI (Graphical User Interface) screen displayed on the display 313. Obviously, a reading report may be also entered by sound or the like by the reading terminal 31.

The reading support server 32 acquires the reading report entered by the reading doctor by using the reading terminal 31 via the network 40 and accumulates (stores) it as data in a symptom database 321. The reading support server 32 structures the reading report at the time of storing the reading report into the symptom database 321. The reading support server 32 acquires the structured data included in the image to be read via the network 40 as electronized-information input means and accumulates it together with the reading report in the symptom database 321. Herein, the reading report corresponds to the medical information MI1, and the structured data included in the image to be read corresponds to the medical information MI2.

In addition, the reading support server 32 generates support information for supporting entry of the reading report by the reading doctor in the reading terminal 31 and outputs it to the reading terminal 31 via the network 40. In the reading support server 32, a reading support program 322 for generating support information is installed. The more detailed configuration of the reading support server 32 will be described later.

In the reading support system 30, desirably, a WWW (World Wide Web) server is mounted on the reading support server 32 and a WWW browser is installed on the reading terminal 31. By transferring an HTML (Hyper Text Markup Language) source describing a GUI screen for entering a reading report from the reading support server 32 to the reading terminal 31, the GUI screen for entering a reading report is displayed on the display 313 and environments of entering a reading report are provided to the reading doctor. Obviously, the WWW server may be installed on a computer physically apart from the reading support server 32. It is not essential to provide the WWW-based input environments, and other methods may be used.

2.2. Configuration of Reading Support Server

FIG. 3 is a block diagram which illustrates a more detailed configuration of the reading support server 32. A structuring unit 333 (a morphological analyzer 334, a class specifying unit 335, and a thesaurus code determining unit 336) and a support information generator 337 in FIG. 3 are functional blocks expressing functions realized when the reading support server 32 as a computer executes the reading support program 322.

As illustrated in FIG. 3, the reading support server 32 has the symptom database 321, the structuring unit 333 for structuring a reading report transferred from the reading terminal 31, and the support information generator 337 for generating support information that supports entry of a reading report by a reading doctor, and also holds a dictionary 338 for structuring which is used for structuring in the structuring unit 333 and a medical thesaurus dictionary 339.

Dictionary for Structuring

The dictionary 338 for structuring is a dictionary in which a medical word and a class of the medical word are registered. The kinds of classes registered in the dictionary 338 for structuring are not limited but, for example, "region (REGION)", "symptom (SYMPTOM)", "diagnosis (DIAGNOSIS)", "inspection (INSPECTION)", and the like can be properly registered.

Medical Thesaurus Dictionary

Figures 4, 5:
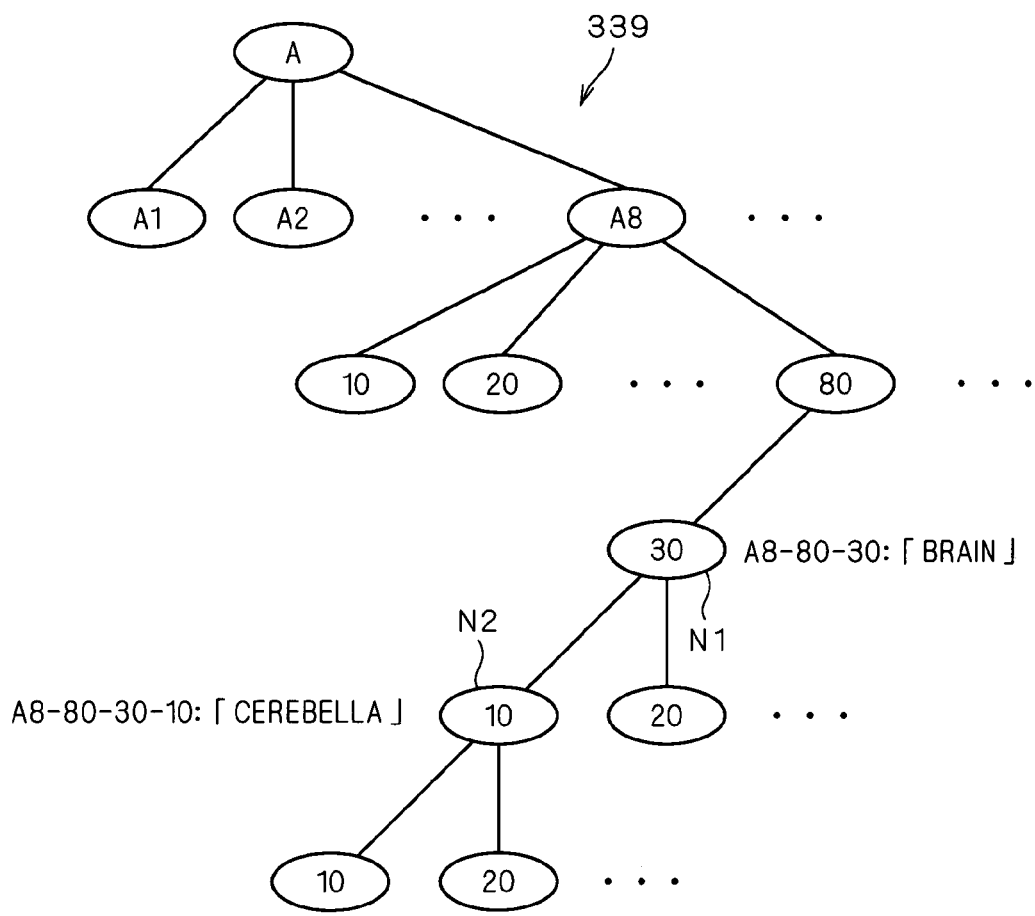
FIG. 4 illustrates a hierarchical structure of a medical thesaurus dictionary.
FIG. 5 illustrates an example of structured data of a reading example report.

As illustrated in FIG. 4, in the medical thesaurus dictionary (hereinafter, simply referred to as "thesaurus") 339 as ontologies describing information of the relations among medical words, words are systemized on the basis of a superior-subordinate relationship in terms of concept. Words are organized hierarchically in such a manner that a word which is high in concept (upper word) is positioned high in a hierarchical structure and a word which is low in concept (lower word) is positioned low in the hierarchical structure. For example, a word "brain" is assigned to a node N1 in the thesaurus 339, and a word "cerebella" as a lower word of "brain" is assigned to a node N2 at a level lower than the node N1 by one.

Further, in the thesaurus 339, a position in a hierarchical structure (hereinafter, simply referred to as "hierarchical position") is specified by a thesaurus code as a code given in accordance with a predetermined rule. The thesaurus code is obtained by, for example, connecting indexes of alphanumeric characters identifying a position at the same level (alphanumeric characters written in ovals indicative of nodes in FIG. 4) by a hyphen (-) indicative of shift among levels. In the thesaurus 339, the hierarchical position of the word "brain" is expressed by a thesaurus code "A8-80-30" and that of the word "cerebella" is expressed by a thesaurus code "A-80-30-10".

Structuring Unit

As illustrated in FIG. 3, the structuring unit 333 has the morphological analyzer 334, the class specifying unit 335, and a thesaurus code determining unit 336.

The morphological analyzer 334 divides a reading report written in a natural sentence into words (morphemes).

The class specifying unit 335 specifies the class of a word obtained by the morphological analyzer 334 with reference to the dictionary 338 for structuring and generates structured data SD1 of the reading report. The structured data SD1 is structured data including elements having medical attributes such as "region", "symptom", "diagnosis", and "inspection".

The thesaurus code determining unit 336 determines a thesaurus code expressing the hierarchical position of data (word) of the element having the attribute of "region" included in the structured data SD1 of the reading report with reference to the thesaurus 339.

Herein, determination of a thesaurus code will be described in more detail.

The thesaurus code determining unit 336 acquires the data (word) of the element having the attribute of "region" included in the structured data SD1 of the reading report and makes a search whether the word is included in the thesaurus 339 or not. When the word is included in the thesaurus 339, the thesaurus code determining unit 336 determines the thesaurus code of the word directly from the search result. On the other hand, in the case where the word is not included in the thesaurus 339, the thesaurus code determining unit 336 estimates a thesaurus code of the word.

At the time of estimating the thesaurus code, morphological analysis is further conducted on the word to be estimated (hereinafter, referred to as "target word"). In the case where the target word cannot be divided into a plurality of words, the thesaurus code determining unit 336 determines that it is impossible to estimate a thesaurus code and finishes estimating the thesaurus code.

On the other hand, when the target word can be divided into a plurality of words, the thesaurus code determining unit 336 makes a search whether the plurality of words are included in the thesaurus 339 or not. When the plurality of words are not included in the thesaurus 339, the thesaurus code determining unit 336 determines that it is impossible to estimate a thesaurus code and finishes estimating a thesaurus code.

In the case where the number of words included in the thesaurus 339 out of the plurality of words is one, the thesaurus code determining unit 336 assumes that the hierarchical position just below the hierarchical position of the one word as a hierarchical position of the target position and determines the thesaurus code of the target position.

In the case where the number of words included in the thesaurus 339 out of the plurality of words is two or more, the thesaurus code determining unit 336 assumes that the hierarchical position just below the hierarchical position of the last word of the two or more words as the hierarchical position of the target word and determines the thesaurus code of the target word.

Estimation of a thesaurus code will be described by a more concrete example. For example, when a word "left-cerebra" is not included in the thesaurus 399, the word "left-cerebra" is divided into two words of "left" and "cerebra" and the thesaurus code determining unit 336 makes a search whether each of "left" and "cerebra" is included in the thesaurus 339 or not. In the case where only "cerebra" as one of the two words is included in the thesaurus 339 and the thesaurus code of the "cerebra" is "A-80-30-20", the thesaurus code determining unit 336 determines the thesaurus code of the word "left-cerebra" as "A-80-30-20-20" indicative of a lower word of the "cerebra" (indicating that the hierarchical position is lower than that of the word "cerebra").

Support Information Generator

The support information generator 337 searches the symptom database 321 by using a search key (query) based on the structured data SD1 of the reading report being entered by the reading doctor with the reading terminal 31 or the structured data SD2 included in an image to be read and transmits support information in which the search result is reflected to the reading terminal 31. More concretely, the support information generator 337 acquires the attribute and element data of a predetermined element included in the structured data SD1 and SD2 and searches the symptom database 321 with the attribute or the element data as a search key. Herein, since the element data as a search key is a character string generated on the basis of structured data included in the reading report or the image to be read, the support information generator 337 searches the symptom database 321 with a character string generated on the basis of medical information being entered as a search key and generates support information on the basis of the search result. As a result, the support information generator 337 can generate support information related to the medical information being entered, so that proper support information can be generated.

2.3. Data Structure

In the following, the data structures of the structured data SD1 of a reading report, the structured data SD2 included in an image to be read, and the structured data SD3 accumulated in the symptom database 321 will be described by using concrete examples.

Concrete Example of Structured Data of Reading Report

Herein, the structured data SD1 of a reading report in the case, as an example, where a reading report describing that "shade is seen in the lung" is given to the structuring unit 333 will be described.

In the structuring unit 333, first, the morphological analyzer 334 divides the reading report that "shade is seen in the lung" into six words of "shade", "is", "seen", "in", "the", and "lung", and the class specifying unit 335 specifies, for example, the class of "lung" as "region" and the class of "shade" as "symptom" as illustrated in the table of FIG. 5. Although the case where only "region" and "symptom" are included as the classes specified by the class specifying unit 335 has been described, there is also a case that other classes such as "diagnosis" and "inspection" are included in the specification result. In such a manner, the reading report is structured as the structured data SD1 including an element having an attribute corresponding to a class.

Concrete Example of Structured Data Included in Image to be Read

The structured data SD2 included in the image to be read is structured data including elements having attributes such as "the name of a patient (PATIENT_NAME)", "the age of a patient (PATIENT_AGE)", "the sex of a patient (PATIENT_SEX)", "inspection (INSPECTION)", "the name of a reading physician (READING_PHYSICIANS_NAME)", "date of reading "READING_DATE"", and "reading time "READING_TIME"". The structured data SD2 may include information of the image diagnostic apparatus 10 and a region.

Structured Data Accumulated in Symptom Database

Figure 6:
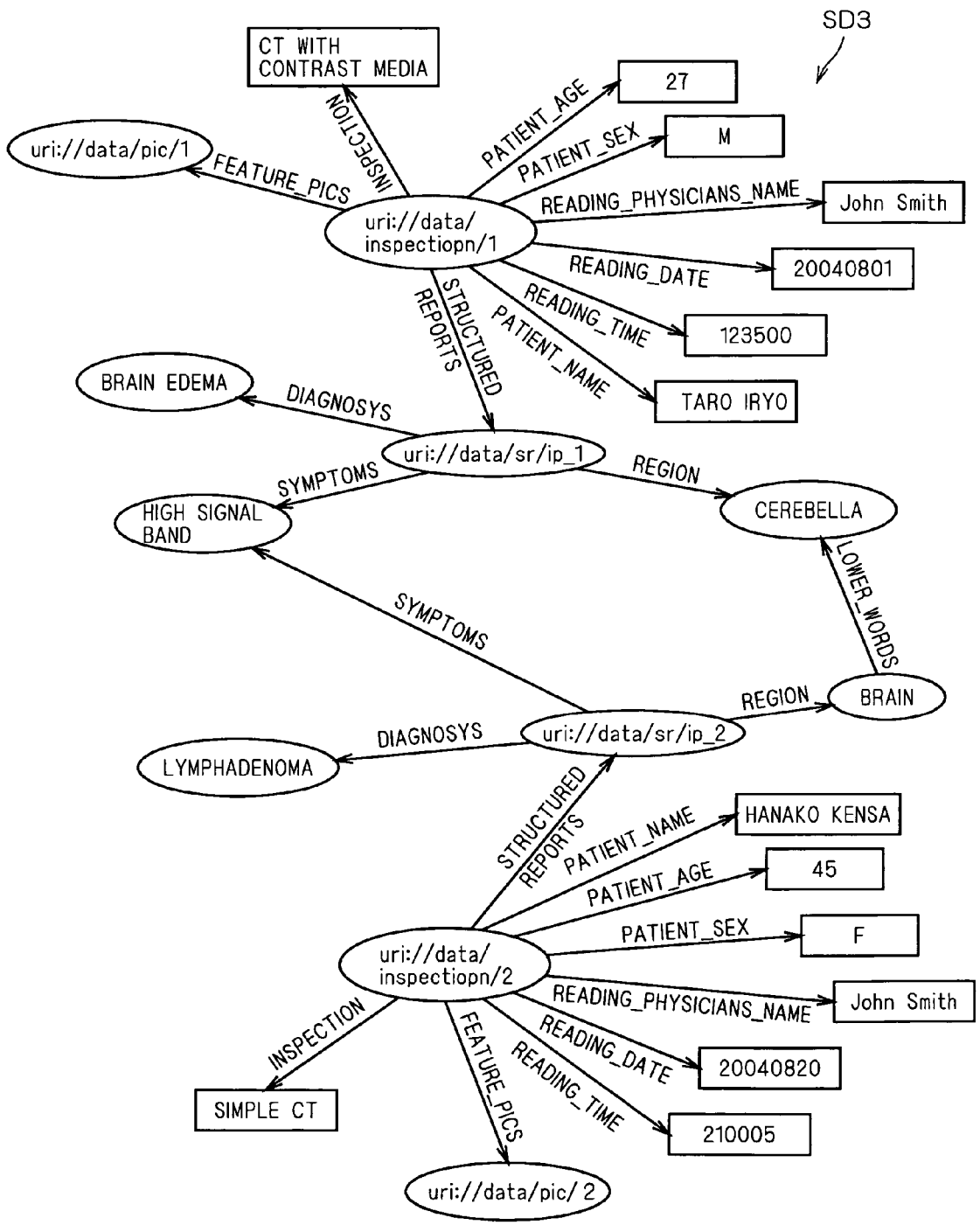
FIG. 6 illustrates an example of structured data accumulated in a symptom database.

FIG. 6 illustrates an example of the structured data SD3 accumulated in the symptom database 321. FIG. 6 illustrates an example of the structured data including two reading reports of images obtained by two inspections (image capturing by the image diagnostic apparatus 10).

As illustrated in FIG. 6, the structured data SD3 accumulated in the symptom database 321 is stated in the RDF (Resource Description Framework) language. In FIG. 6, a plurality of ovals indicate resources in the RDF and a plurality of rectangles indicate literals in the RDF. In FIG. 6, in two elements connected by an arc (arrow), the resource at the start point of the arc is also called a subject and the resource or literal at the end point of the arc is also called an object. By employing statement in the RDF language, changing of the data structure is facilitated.

In the structured data SD3, an inspection is expressed by an URI (Uniform Resource Identifier). Therefore, the structured data SD3 includes two URIs (uri://data/inspection1, and uri://data/inspection/2) corresponding to two inspections.

Further, in the structured data SD3, the reading report is also expressed by an URI. Therefore, the structured data SD3 includes two URIs (uri://data/sr/ip_1 and uri://data/sr/ip_2) corresponding to two reading reports.

A URI expressing an inspection and a URI expressing a reading report on an image obtained by the inspection are connected via an arc using the URI expressing the inspection as the start point and the URI expressing the reading report as the end point. To the arc, "STRUCTURED_REPORTS" is given as a property in the RDF. By the operation, in the structured data SD3, the reading report and the inspection are associated with each other.

Further, in the structured data SD3, to the URI expressing the inspection, elements having attributes of "the name of a patient (PATIENT_NAME)", "the age of a patient (PATIENT_AGE)", "the sex of a patient (PATIENT_SEX)", "inspection (INSPECTION)", "the name of a reading physician (READING_PHYSICIANS_NAME)", "date of reading "READING_DATE"", and "reading time "READING_TIME"" are connected.

In addition, to the URI expressing the inspection, an image featuring the inspection is added as the element having the attribute "FEATURED_PICS". This image is also expressed by the URI "uri://data/pic/1 and uri://data/pic/2).

Further, in the structured data SD3, to the URI expressing the reading report, the elements having attributes of "region (REGION)", "symptom (SYMPTOM)", and "diagnosis (DIAGNOSIS)" are connected. The elements connected to the URI are elements included in the structured data SD1 and SD2 but all of elements included in the structured data SD1 and SD2 do not have to be included in the structured data SD3. Elements which are not included in the structured data SD1 and SD2 may be also included in the structured data SD3.

The structured data SD3 is subjected to a process of making elements whose element data overlaps commonly used. For example, as illustrated in FIG. 6, the element (resource) of "high signal band" having the attribute of "symptom (SYMPTOM)" is connected to two URIs expressing reading reports and commonly used.

In the structured data SD3, the relation between elements having the attribute of "region (REGION)" is specified by the thesaurus code and reflected in the data structure. For example, from the thesaurus code, "cerebella" as the element having the attribute of "region (REGION)" of the URI of uri://data/sr/ip_1 can be specified as a lower word of "brain" of the element having the attribute of "region (REGION)" of the URI of uri://data/sr/ip_2. Consequently, "cerebella" is the object having the attribute of "lower word (LOWER_WORD)" of the object of "brain". In such a manner, the thesaurus 339 held by the reading support system 30, that is, the ontology is reflected in the data structure of the structured data SD3 stored in the symptom database 321.

3. Reading Terminal Operation Procedure and GUI Screen

Figure 7:
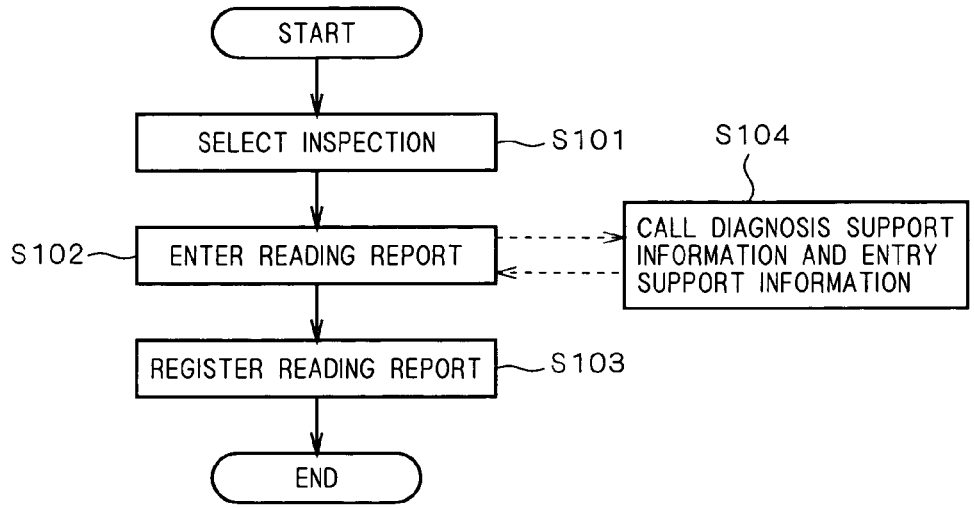
FIG. 7 is a flowchart which shows an operation procedure of a reading terminal.

In the following, the procedure of operating the reading terminal 31 in the case where the reading doctor enters a reading report and a GUI screen displayed on the display 313 in the case where the reading doctor enters a reading report will be described with reference to FIGS. 7 to 17. FIG. 7 is a flowchart which shows the operation procedure of the reading terminal 31, and FIGS. 8 to 17 illustrate examples of the GUI screen displayed on the display 313.

Selection of Inspection (Step S101)

Figure 8:
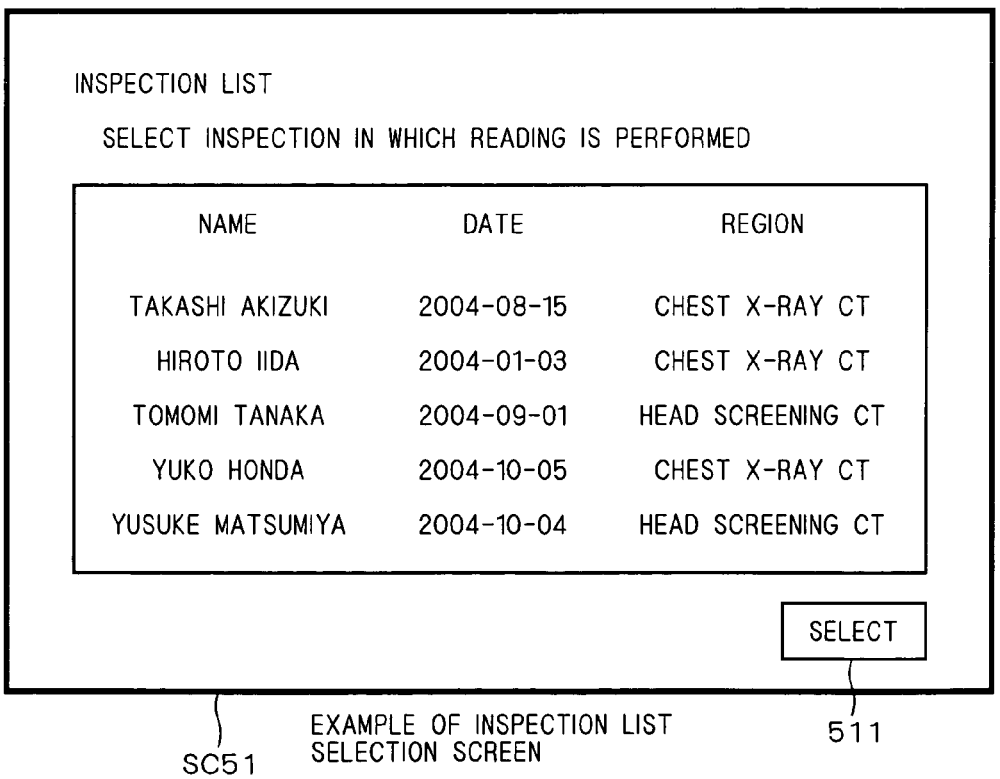
FIG. 8 illustrates an example of an inspection list selection screen.

In the operation of the reading terminal 31, first, an inspection in which reading is performed is selected by using an inspection list selection screen SC51 in FIG. 8. As illustrated in FIG. 8, in the inspection list selection screen SC51, a list of information specifying an inspection such as name, date, and region is displayed. A reading doctor can select an inspection in which reading is performed by selecting one of inspections displayed in the list and clicking a selection button 511.

Entry of Reading Report (Step S102)

Figure 9:
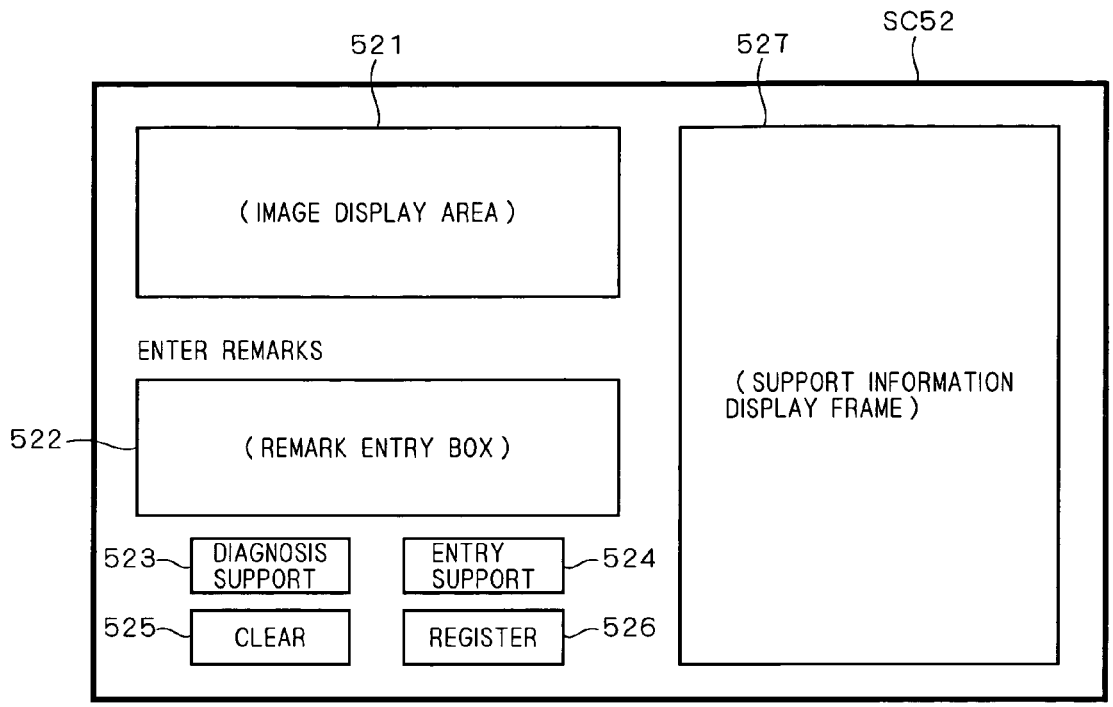
FIG. 9 illustrates an example of a reading report entry screen.
Figure 10:
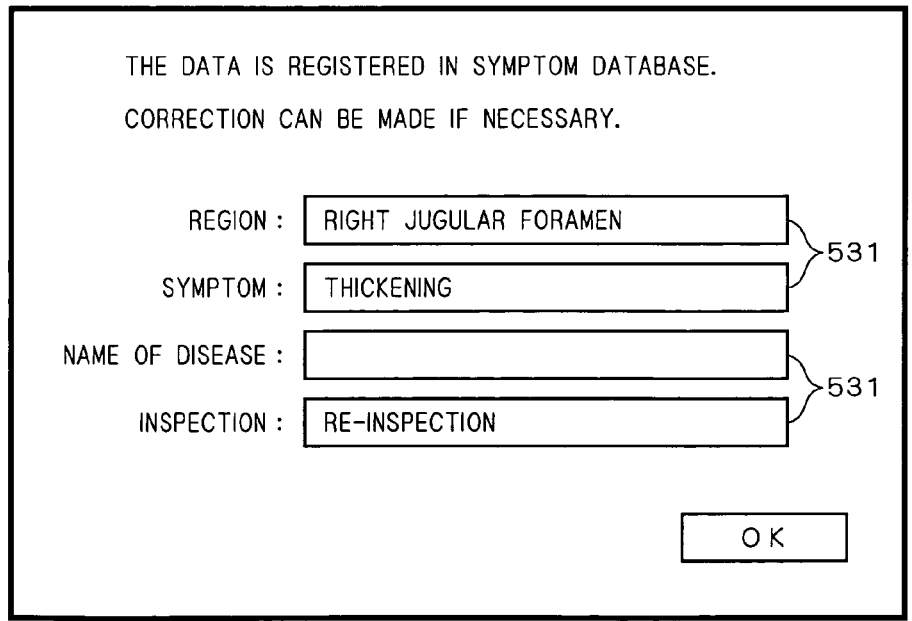
FIG. 10 illustrates an example of a registration data confirmation screen.

After selection of an inspection in which reading is performed, in the reading terminal 31, a reading report is entered by using a reading report entry screen SC52 of FIG. 9. As illustrated in FIG. 9, the reading report entry screen SC52 has an image display area 521, a remark entry box 522, a diagnosis support button 523, an entry support button 524, a clear button 525, a registration button 526, and a support information display frame 527. A character string entered in the remark entry box 522 is a reading report. A reading doctor can enter a reading report by performing reading while seeing an image to be read that is displayed in the image display area 521 and entering the result of reading in the form of a natural sentence (character string) in the remark entry column 522. In the image display area, a single image or a plurality of images to be read related to the inspection selected on the inspection list selection screen SC51 is/are displayed in a desired size.

Registration of Reading Report (Step S103)

After completion of entry of the reading report, the reading doctor can give an instruction to accumulate the entered reading report in the symptom database 321 to the reading support system 30 by clicking the registration button 526 in the reading report entry screen SC52.

In the reading support system 30, the reading report is converted to the structured data SD1 prior to accumulation to the symptom database 321. Prior to execution of an accumulation instruction, a registration data confirmation screen SC53 (FIG. 10) for correcting the data of the element of the structured data SD1 is displayed on the display 313. The registration data confirmation screen SC53 includes element data display boxes 531, and data of an element displayed in the element data display box 531 can be corrected by a reading doctor.

Calling of Diagnosis Support Information and Entry Support Information (Step S104)

During entry of a reading report (step S102), that is, until the registration button 526 is clicked in the reading report entry screen SC52, the reading doctor can call diagnosis support information or entry support information into the support information display frame 527.

Figure 11:
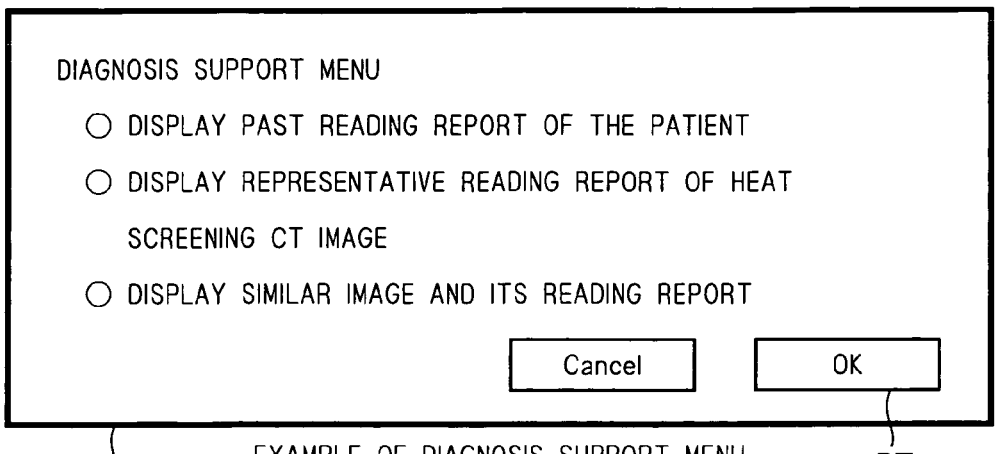
FIG. 11 illustrates an example of a diagnosis support menu for calling diagnosis support information.
Figure 12:
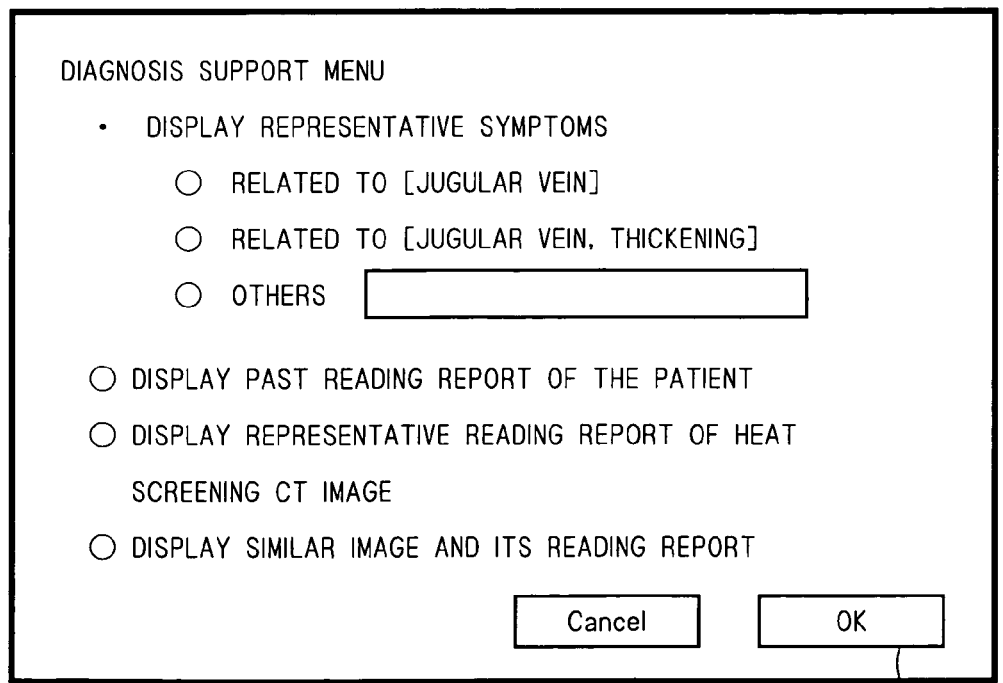
FIG. 12 illustrates an example of the diagnosis support menu for calling diagnosis support information.

FIGS. 11 and 12 illustrate examples of diagnosis support menus MN11 and MN12 for calling diagnosis support information. The diagnosis support menus MN11 and MN12 are called into the support information display frame 527 by clicking the diagnosis support button 523 on the reading report entry screen SC52. Obviously, the diagnosis support menus MN11 and MN12 may be called by another operation. FIG. 11 corresponds to an example of the diagnosis support menu called in a state where no data is entered in the remark entry box 522, and FIG. 12 corresponds to an example of the diagnosis support menu called in a state where data is entered in the remark entry box 522.

As illustrated in FIG. 11, from the diagnosis support menu MN11, (1) a past reading report of a patient related to an image to be read (refer to the diagnosis support information INF11 in FIG. 13), (2) a representative reading report of an image obtained by the same inspection as that performed on the image to be read (refer to the diagnosis support information INF12 in FIG. 14), or (3) an image similar to the image to be read and the reading report of the similar image (refer to the diagnosis support information INF13 in FIG. 15) can be selected and called as the diagnosis support information. The concrete data of the diagnosis support menu MN11 changes according to the kind of an inspection by which an image to be read is acquired, and the diagnosis support menu MN11 is an example of the diagnosis support menu displayed in the case of reading a head screening CT image.

As illustrated in FIG. 12, from the diagnosis support menu MN12, any of the reading reports (1) to (3) similar to those of the diagnosis support menu MN11, in addition, (4) a reading report related to "carotid artery" (refer to the diagnosis support information INF14 in FIG. 16), (5) a reading report related to "jugular vein, thickening", and (6) a reading report related to an arbitrary symptom other than the above can be selectively called as the diagnosis support information. Concrete data of the diagnosis support menu also changes according to the kind of an inspection by which the image to be read is captured and, in addition, the reading report entered in the remark entry box 522.

In FIGS. 13 to 16, by selecting one of the reading reports displayed in a list and clicking a detail display button BT, more detailed diagnosis support information such as full text of a reading report or the like is displayed in the support information display frame 527.

Figure 17:
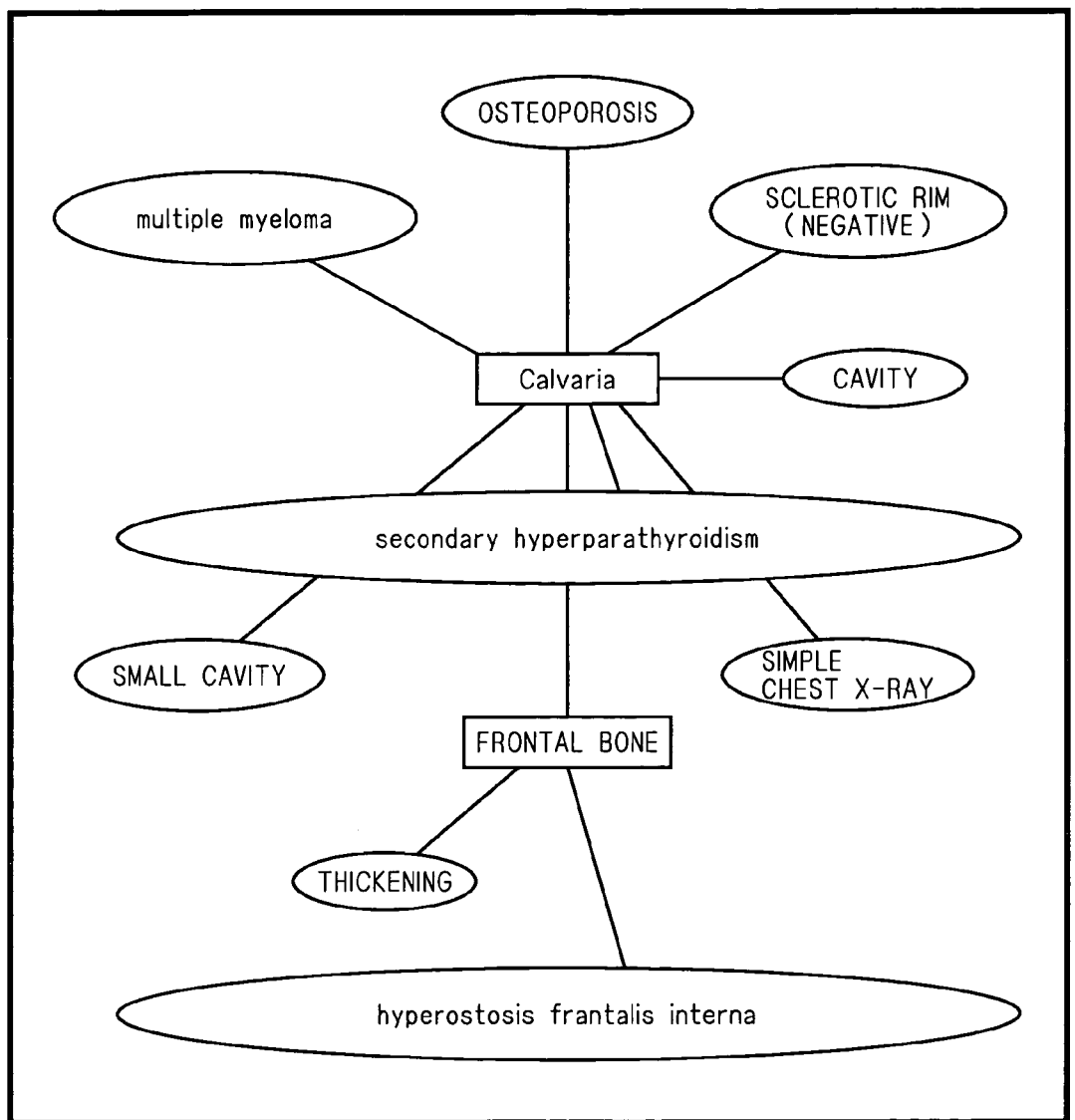
FIG. 17 illustrates an example of entry support information.

FIG. 17 illustrates an example of entry support information INF15 called when the entry support button 524 is clicked on the reading report entry screen SC52.

The entry support information INF15 is given as a graph obtained by connecting a plurality of elements. In the graph, a plurality of words assigned to a plurality of nodes each expressed in rectangular shape have the relation of high and low orders in concept. The display mode of the entry support information INF15 is not limited to the above but may be a mode such as a list of a plurality of words. However, by giving the entry support information INF15 in the form of a graph, there is an advantage such that the relations among elements can be easily grasped.

The reading doctor can transfer the data of elements in the graph into the remark entry box 522 by a predetermined GUI operation such as clicking.

4. Operation of Reading Support System

In the following, operations of the reading support system 30 in the case (a) of accumulating a reading report into the symptom database 321, the case (b) of generating the diagnosis support information INF11 to INF14, and the case (c) of generating the entry support information INF15 will be described.

4.1. Operation in the Case of Accumulating Reading Report Data into Symptom Database FIG. 18 is a flowchart which shows an operation of the reading support system 30 in the case of accumulating a reading report into the symptom database 321. The operation starts in response to click of the registration button 526 in the reading report entry screen SC52 as a trigger.

As shown in FIG. 18, when the registration button 526 is clicked on the reading report entry screen SC52, first, a reading report entered in the remark entry box 522 is transferred as data from the reading terminal 31 to the reading support server 32 (step S201) and is structured by the structuring unit 333, thereby generating the structured data SD1 of the reading report (step S202).

Subsequently, the structured data SD2 included in the image to be read is transferred from the image server 20 to the reading support server 32 (step S203), and concrete data such as "name of reading doctor", "reading date", and "reading time" is added to elements having attributes regarding reading (step S204).

In steps S201 to S204, the reading support server 32 acquires the structured data SD1 and SD2 to be additionally accumulated in the symptom database 321. In step S205 subsequent to step S204, a process of adding the acquired structured data SD1 and SD2 to the structured data SD3 already accumulated in the symptom database 321 is performed and, after that, the operation flow is finished.

4.2. Operation in the Case of Generating Diagnosis Support Information

FIG. 19 is a flowchart which shows an operation of the reading support system 30 in the case of generating diagnosis support information. The operation starts in response to click of the diagnosis support button 523 in the reading report entry screen SC52 as a trigger.

As shown in FIG. 19, when the diagnosis support button 523 is clicked on the reading report entry screen SC52, the reading report is transferred from the reading terminal 31 to the reading support server 32 in step S301 similar to step S201. In steps S302 and S303 similar to steps S203 and S204, the reading support server 32 acquires the structured data SD2 included in the image to be read.

As described above, at the time of presenting the diagnosis support information, the diagnosis support menu which varies depending on the presence/absence of entry of data to the remark entry box 522 is provided. Consequently, in step S304 subsequent to step S303, the process is branched according to the presence or absence of entry of data to the remark entry box 522, that is, whether the reading report acquired in step S301 is empty data or not.

In the case where it is determined that no data is entered to the remark entry box 522 in step S304, the support information generator 337 generates the diagnosis support menu MN11 based on the structured data SD2 included in the image to be read (step S305). More specifically, the support information generator 337 acquires the data of the element having a predetermined attribute in the structured data SD2 included in the image to be read, and searches the symptom database 321 with the attribute and the acquired element data as a search key to retrieve an element whose attribute and element data matching the search key. For example, in the case where the element of data of "Yusuke Matsumiya" having the attribute of "the name of a patient "PATIENT_NAME")" exists in the structured data SD2 included in the image to be read, the support information generator 337 searches the symptom database 321 for an element having the attribute that is "the name of a patient (PATIENT_NAME)" and having the element data that is "Yusuke Matsumiya". The support information generator 337 forms a list of inspections as subjects of elements extracted by the search and includes means for calling (such as hyper link) the list (part of the diagnosis support information) in the diagnosis support menu MN11. Obviously, similar process may be performed on an element having other attributes.

On the other hand, when it is determined in step S304 that data is entered in the remark entry box 522, the reading report is structured by the structuring unit 333 and the structured data SD1 of the reading report is generated (step S306). After that, the support information generator 337 generates the diagnosis support menu MN12 based on the structured data SD1 of the reading report and the structured data SD2 included in the image to be read (step S307). More specifically, the support information generator 337 acquires the data of the element having a predetermined attribute in the structured data SD1 of the reading report and searches the symptom database 321 by using the attribute and the acquired element data as a search key, for an element having an attribute and element data matching the search key. For example, in the case where the structured data SD1 of the reading report includes an element having data of "carotid artery" whose attribute is "region", the support information generator 337 searches the symptom database 321 for an element having the attribute "region" and the element data of "carotid artery". The support information generator 337 forms a list of inspections as subjects of elements extracted by the search and includes means for calling the list in the diagnosis support menu MN12. The diagnosis support menu MN12 concurrently includes the calling means described in step S305. Obviously, similar process may be performed on an element having other attributes in step S307.

After generation of the diagnosis support menu in step S305 or S307, the reading support server 32 transmits the generated diagnosis support menu MN11 or MN12 to the reading terminal 31 (step S308) and, after that, the operation flow is finished.

Since the structured data SD1 and SD2 of the reading report includes an element having an attribute related to medical care, the diagnosis support information INF11 to INF14 include information having an attribute related to medical care.

4.3. Operation in the Case of Generating Entry Support Information

FIG. 20 is a flowchart which shows an operation of the reading support system 30 in the case of generating entry support information. The operation starts in response to click of the entry support button 524 in the reading report entry screen SC52 as a trigger.

As shown in FIG. 20, when the entry support button 524 is clicked on the reading report entry screen SC52, a reading report is transferred from the reading terminal 31 to the reading support server 32 in steps S401 and S402 similar to steps S201 and S202 (step S401) and is structured by the structuring unit 333 (step S402).

Subsequently, the support information generator 337 acquires the attribute and the element data of an element included in the structured data SD1 of the reading report and searches the reading support server 32 by using the acquired attribute and element data as a search key, for an element whose attribute and element data matching the search key (step S403).

In step S404 subsequent to step S403, the process is branched depending on whether the element whose attribute and element data matching the search key is extracted or not in step S403.

In the case where an element whose attribute and element data match with the search key is not extracted in step S404, a process of estimating a thesaurus code is performed on the element data acquired in step S403 and, after that, the program moves to step S406 (step S405).

On the other hand, in the case where an element whose attribute and element data match with the search key is extracted in step S404, the program moves to step S406 without performing the process in step S405.

Subsequently, the element data of the element extracted in step S403 or an element related to the thesaurus code estimated in step S405 is acquired (step S406) and the acquired element data is output (step S407). An element related to the element extracted in step S403 is, for example, an element having a distance from the extracted element in the data structure, that is within a predetermined range (the hierarchical range is a predetermined range). An element related to the estimated thesaurus code is an element that is in a close hierarchical position from the extracted element in the medical thesaurus dictionary 339 or an element having a distance from the element in the data structure, that is within a predetermined range.

Since the thesaurus as ontology is reflected in the data structure of the structured data SD3 from which the entry support information INF15 is extracted, at the time of generating the entry support information INF15, the ontology held by the reading support system 30 is used. Since information of the relations among medical words included in the ontology is reflected in the entry support information INF15, proper support information can be generated.

5. Modifications

Modification on Reading Support System

Although the example in which the reading support system 30 is part of the medical image management system 1A has been described in the foregoing preferred embodiment, the reading support system 30 may be part of various medical systems such as a radiology information system (RIS) and a hospital information system (HIS). The reading support system 30 may be also used independently of other systems.

Modification on Image Viewer

Although the example in which the reading report entry screen SC52 includes the function of an image viewer has been described in the foregoing preferred embodiment, alternatively, an independent image viewer may be used for reading an image.

Modification on Medical Information

Although the mode of using the order information in the structured data SD2 included in an image to be read for generation of support information has been described in the foregoing preferred embodiment, it is also possible to generate support information INF11 to INF15 on the basis of only a reading report or on the basis of information other than the order information. The information as the base of the support information INF11 to INF15 may be character string information of an image to be read and does not have to be structured data included in the image to be read. For example, the support information INF11 to INF15 may be generated on the basis of information obtained by performing an imaging process on an image. Character string information which is not structured can be structured in the reading support server 32 in a manner similar to the operation performed on the reading report.

Modification on Structuring

Although the example of structuring a reading report by dividing a natural sentence into words and specifying a class with reference to the dictionary 338 for structuring has been described in the foregoing preferred embodiment, a reading report may be structured by a method other than the above.

While the invention has been shown and described in detail, the foregoing description is in all aspects illustrative and not restrictive. It is therefore understood that numerous modifications and variations can be devised without departing from the scope of the invention.

What is claimed is:

1. A medical support system comprising:
    an input unit used for entering medical information;
    a storage for storing the medical information entered by using said input unit;
    a structuring unit for:
        receiving the medical information entered by using said input unit; and
        structuring the medical information into structured medical information wherein the structured medical information comprises:
            an element that represents an individual word of the medical information;
            an attribute that categorizes the element and is assignable to the element; wherein:
                the attribute is determined based on a preregistered class;
                the element is associated with the attribute; and
                the element is assigned a hierarchical position according to the attribute associated with the element;
    a generator for generating support information that supports entry of medical information by a medical professional in said input unit, wherein
    said generator generates said support information on the basis of the structured medical information.

2. The medical support system according to claim 1, wherein the medical information comprises character string information.

3. The medical support system according to claim 1, wherein said generator generates said support information on the basis of character string information that describes an image acquired by an image diagnostic apparatus.

4. The medical support system according to claim 1, wherein the attribute associated with the element is an attribute related to medical care.

5. The medical support system according to claim 4, wherein said structured data is stated in a Resource Description Framework language.

6. The medical support system according to claim 1, wherein search for medical information stored in said storage is performed by using, as a search key, a character string generated on the basis of medical information being entered in said input unit, and said support information is generated on the basis of a result of the search.

7. The medical support system according to claim 1, wherein:
    the storage is for further storing an ontology describing relations among words; and
    said support information is generated from said ontology.

8. The medical support system according to claim 7, wherein said ontology is a medical thesaurus dictionary.

9. The medical support system according to claim 1, wherein said medical information includes a reading report describing a result of reading of an image for medical use by a doctor.

10. The medical support system according to claim 1, wherein said medical information includes a nursing report in which nursing activities of a nurse are recorded.

11. The medical support system according to claim 1, wherein said medical information includes an incident report in which an incident which occurs during medical activities is recorded.

12. The medical support system according to claim 1, wherein said medical information includes a diagnosis report in which a result of diagnosis by a doctor is described.

13. The medical support system according to claim 1, wherein said support information is a graph in which a plurality of elements are connected.

14. The medical support system according to claim 1, wherein the structuring unit comprises a morphological analyzer for dividing the medical information entered by using said input unit into at least one morpheme.

15. The medical support system according to claim 14, wherein:
the element of the structured medical information comprises the at least one morpheme; and
the structuring unit further comprises a class specifying unit for classifying the element according to the preregistered class.

16. The medical support system according to claim 1, further comprising:
a thesaurus dictionary comprising:
an ontology of words organized in a hierarchy comprising:
a superior word node representing a superior word that is high in concept; and
a subordinate word node representing:
a subordinate word that:
is lower in concept than the superior word; and
subordinate to the superior word; wherein:
the superior word node is assigned a first thesaurus code that represents the hierarchical position of the superior word node in the ontology; and
the subordinate word node is assigned a second thesaurus code that represents the hierarchical position of the subordinate word node in the ontology.

17. The medical support system according to claim 16, further comprising:
a thesaurus code determining unit for assigning a third thesaurus code to the element of the structured medical information, wherein assigning a third thesaurus code comprises:
searching the ontology of words organized in the hierarchy;
when the element matches the superior word of the superior word node, assigning the first thesaurus code as the third thesaurus code;
when the element matches the subordinate word of the subordinate word node, assigning the second thesaurus code as the third thesaurus code; and
when the element does not match the superior word or the subordinate word, assigning an estimated thesaurus code as the third thesaurus code.

18. The medical support system according to claim 1, further comprising:
a symptom database for storing structured medical symptom information, wherein the medical symptom information comprises:
an inspection grouping that defines an inspection, wherein the inspection grouping comprises:
an inspection resource node that represents an inspection image of a patient;
a inspection literal node that represents a literal value from the inspection image; and
an inspection attribute arc connecting the inspection resource node with the inspection literal node that represents an attribute of the inspection resource node having the literal value represented by the inspection literal node;
a reading report grouping that defines a reading report of the inspection image of the patient, wherein the reading report grouping comprises:
a reading report resource node that represents a reading report;
a reading report element resource node that represents an element of the reading report; and
a reporting report attribute arc connecting the reading report resource node with the reading report element resource node that represents an attribute of the reading report having the element represented by the reading report element resource node; and
a reading report relationship arc associating the inspection grouping with the reading report grouping;
wherein the generator for generating support information further generates the support information by searching the medical symptom information with a character string selected from the structured medical information.

* * * * *